United States Patent [19]

Yokoyama et al.

[11] 4,444,743

[45] Apr. 24, 1984

[54] RADIOACTIVE DIAGNOSTIC AGENT AND ITS PREPARATION

[75] Inventors: Akira Yokoyama, Otsu; Hisashi Tanaka, Ashiya; Akira Yamada; Yasushi Arano, both of Kyoto, all of Japan

[73] Assignee: Nihon Medi-Physics Co., Ltd., Hyogo, Japan

[21] Appl. No.: 302,563

[22] Filed: Sep. 15, 1981

[51] Int. Cl.³ .................... A61K 43/00; A61K 49/00
[52] U.S. Cl. .................................. 424/1.1; 564/19; 424/9
[58] Field of Search ............... 564/19; 424/1, 1.5, 424/9

[56] References Cited

U.S. PATENT DOCUMENTS

| | | | |
|---|---|---|---|
| 3,478,035 | 11/1969 | Barrett | 564/19 |
| 3,478,036 | 11/1969 | Winkelman et al. | 564/19 |
| 4,031,198 | 6/1977 | Jackson et al. | 424/1 |
| 4,284,619 | 8/1981 | Lin | 424/1 |
| 4,338,248 | 7/1982 | Yokoyama et al. | 424/1 |

OTHER PUBLICATIONS

De Kieviet, J. Nucl. Med., 22i 703–709 (1981).
Goodman et al., Chemical Abstracts 94 (1981), #116892n.

*Primary Examiner*—Christine M. Nucker
*Attorney, Agent, or Firm*—Birch, Stewart, Kolasch & Birch

[57] ABSTRACT

A radioactive diagnostic agent for imaging of various organs, particularly of brain, which comprises a radioactive element such as $^{99m}TC$ and a non-radioactive carrier comprising as the essential component glucosone-bis(thiosemecarbazone) of the formula:

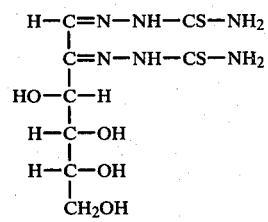

13 Claims, No Drawings

RADIOACTIVE DIAGNOSTIC AGENT AND ITS PREPARATION

The present invention relates to a radioactive diagnostic agent and its preparation. More particularly, it relates to a radioactive element-labeled compound for nuclear medical diagnosis, particularly for diagnosis of brain, and its preparation process.

Radioactive diagnostic agents for nuclear medical diagnosis of brain such as imaging of brain and brain functional study are required to have the following properties: (1) they can pass through a blood-brain barrier to reach the brain; and (2) they can be accumulated in the brain at a high concentration within a short time and stay there over a period of time required for clinical study. In order to find radioactive diagnostic agents satisfying these requirements, various studies have been made. Among them, $^{18}F$-labeled deoxyglucose (Gallagher et al.: J. Nuclear Medicine, Vol. 19, pages 1154–1161 (1978)) and $^{123}I$-labeled phenylalkylamines (Winchell et al.: J. Nuclear Medicine, Vol. 21, pages 940–946 (1980)) are notable from the practical viewpoint. These compounds can pass through a blood-brain barrier to be accumulated in the brain and are evaluated to be practically useful for the purpose of imaging of brain and brain functional study.

However, $^{18}F$ is a positron emitting nuclide, and a special apparatus such as a positron camera is needed for imaging. Thus, ordinary scintillation cameras which are widely employed in the field of nuclear medicine are not usable. Further, the half life of $^{18}F$ is so short as 1.8 hours, and therefore a great limitation is present on the time for manufacture, transportation and supply of the radioactive element or the labeled diagnostic agent. These drawbacks exist inherently in $^{18}F$-labeled deoxyglucose.

On the other hand, $^{123}I$-labeled phenylalkylamines can not give a sufficiently clear image by the use of a collimator for low energy gamma-rays, which is the most frequently employed in scintillation cameras. Further, $^{123}I$ is relatively expensive, and the use of $^{123}I$-labeled phenylaklkylamines in such an amount that can be sufficient for diagnosis is uneconomical.

As a result of the extensive study seeking for any substance suitable as a carrier for radioactive elements in the field of nuclear medicine, it has now been found that glucosone-bis(thiosemicarbazone) (hereinafter referred to as "GBT") of the formula:

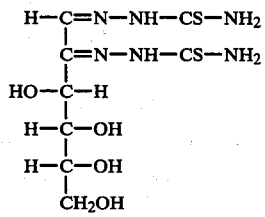

can form stable chelate compounds with various radioactive elements and the resulting chelate compounds (i.e. the radioactive element-labeled compounds) can pass through a blood-brain barrier. It has also been found that the radioactive element-labeled GBT can be used as a radioactive diagnostic agent which makes possible highly reliable diagnosis, particularly in brain.

According to the present invention, there is provided a non-radioactive carrier for a radioactive element to be administered to mammals including human beings for nuclear medical diagnosis, which comprises GBT. There is also provided a radioactive diagnostic agent which comprises a radioactive element and the said non-radioactive carrier.

GBT can be produced, for instance, by oxidizing α-D-glucose with cupric acetate to form a carbonyl group at the 2-position and reacting the resultant glucosone with thiosemicarbazide to introduce thiosemicabazone groups into the 1- and 2-positions.

GBT may be used as a carrier in two different ways depending upon the kind or state of the radioactive element to be carried. When the radioactive element is in a valency state which is not required to be reduced or oxidized for formation of a stable chelate compound, GBT is contacted with the radioactive element in an aqueous medium to obtain a radioactive element-labeled BGT as the chelate compound. This labeling manner may be applied to Gallium-67, Indium-111, etc. When the radioactive element is in a valency state which is required to be reduced or oxidized for formation of a stable chelate compound, GBT is contacted with the radioactive element in an aqueous medium in the presence of a reducing agent or an oxidizing agent to obtain a radioactive element-labeled GBT as the chelate compound. This labeling manner may be applied to Technetium-99m, etc.

Therefore, the non-radioactive carrier of the invention may comprise GBT optionally with a reducing agent or an oxidizing agent for the radioactive element to be used for labeling.

As the reducing agent, there may be usually employed a stannous salt, i.e. a salt of divalent tin ion ($Sn^{++}$). Specific examples are stannous halides (e.g. stannous chloride, stannous fluoride), stannous sulfate, stannous nitrate, stannous acetate, stannous citrate, etc. $Sn^{++}$ ion-bearing resins such as ion-exchange resins charged with $Sn^{++}$ ion are also usable.

In addition to GBT as the essential component and a reducing agent or an oxidizing agent as the optional component, the carrier of the invention may comprise any other additive(s) when desired. Examples of such additive(s) are a pH controlling agent such as an acid, a base or a buffering substance, a reductive stabilizer such as ascorbic acid, erythorbic acid or gentisic acid or its salt, an isotonizing agent such as sodium chloride, a preserving agent such as benzyl alcohol, etc.

On preparation of the non-radioactive carrier of the invention, GBT and, if used, other additives including a reducing agent or an oxidizing agent may be mixed in an optional order. The carrier may be formulated in the form of powdery preparation, particularly of lyophilized powder, or in the form of liquid preparation, particularly of aqueous solution.

For preparation of the radioactive diagnostic agent of the invention, a radioactive element may be contacted with the non-radioactive carrier, usually in an aqueous medium, whereby the radioactive element-labeled radioactive diagnostic agent is prepared in situ. The radioactive element is usually employed in the form of salt, preferably of water-soluble salt, and normally used as an aqueous solution, which may additionally comprise any conventional additive(s) such as an isotonizing agent (e.g. sodium chloride) or a preserving agent (e.g. benzyl alcohol). For instance, technetium-99m is usually available in the form of pertechnetate (wherein $^{99m}Tc$ is heptavalent) and employed as an aqueous solution.

When such aqueous solution is combined with the non-radioactive carrier comprising a reducing agent such as a stannous salt, $^{99m}$Tc is reduced with the reducing agent to the one in a lower valency (i.e. tetravalent) state, and there is obtained a $^{99m}$Tc-labeled radioactive diagnostic agent comprising a chelate compound between GBT and $^{99m}$Tc in a stable state. When the reducing agent in a water-insoluble form such as an ion-exchange resin charged with Sn$^{++}$ ion is used, it is to be eliminated from the resulting radioactive diagnostic agent by an appropriate separation procedure such as filtration prior to its administration.

The radioactive element in the radioactive diagnostic agent should have sufficient radioactivity and radioactivity concentration which can assure reliable diagnosis, although any particular limitation is not present. For instance, in case of the radioactive element being $^{99m}$Tc, the amount of the radioactive diagnostic agent to be administered to a human adult may be from about 0.5 to 5.0 ml, which usually includes a radioactivity of 0.1 to 50 mCi.

The radioactive diagnostic agent of this invention is useful for nuclear medical diagnosis, particularly for imaging of brain and brain functional study.

Practical and presently preferred embodiments of the invention are illustratively shown in the following Examples wherein % is by weight, unless otherwise defined.

EXAMPLE 1

Preparation of glucosone

To a solution of α-D-glucose (4.5 g) in water (10 ml), a solution of cupric acetate (20 g) in methanol (250 ml) was added, and the resultant mixture was heated on a water bath for 1 hour. The reaction mixture was cooled, and the precipitated cuprous oxide was eliminated by filtration. Hydrogen sulfide gas was introduced into the filtrate for about 1 minute to precipitate the unreacted cupric acetate in the form of cupric sulfide. After elimination of the precipitate by filtration, the filtrate was treated with a small amount of activated charcoal and concentrated under reduced pressure to give glucosone in a syrupy state.

EXAMPLE 2

Preparation of glucosone-bis(thiosemicarbazone) (GBT)

To a solution of glucosone obtained in Example 1 in 0.1 N acetic acid (6 ml), a solution of thiosemicarbazide (4.5 g) in water (50 ml) was dropwise added, and the resulting mixture was refluxed for about 1 hour. The reaction mixture was cooled with ice, and the precipitated crystals were collected by filtration and recrystallized from water to give glucosone-bis(thiosemicarbazone) (5 g). M.P. 225° C. (decomp.). Elementary analysis for $C_8H_{16}O_4N_6S_2$ (%): Calcd.: C, 29.62; H, 4.97; O, 19.73; N, 25.91; S, 19.77. Found: C, 29.57; H, 4.88; O, 19.46; N, 26.14; S, 19.70.

EXAMPLE 3

Preparation of the non-radioactive carrier

Glucosone-bis(thiosemicarbazone) obtained in Example 2 was dissolved in a 0.1 M acetate buffer (pH, 5.0) previously eliminated dissolved oxygen therefrom to make a concentration of $10^{-3}$ M. This solution was filtered through a microfilter to eliminate bacteria and filled in an ampoule. After the addition of benzyl alcohol as a preservative thereto to make a 0.9 % concentration, the air above the solution in the ampoule was replaced by nitrogen gas, followed by sealing.

EXAMPLE 4

Preparation of the non-radioactive carrier

Glucosone-bis(thiosemicarbazone) obtained in Example 2 was dissolved in a 0.1 M acetate buffer (pH, 5.0) previously eliminated dissolved oxygen therefrom to make a concentration of $10^{-3}$ M. To the resulting solution (10 ml), an aqueous solution of stannous chloride (4 μg/ml; 10 ml) was added, and the resultant mixture was passed through a microfilter and filled in an ampoule. Benzyl alcohol as a preservative was added thereto to make a concentration of 0.9 %. After replacement of the air above the solution in the ampoule by nitrogen gas, the ampoule was sealed.

EXAMPLE 5

Preparation of the non-radioactive carrier

Glucosone-bis(thiosemicarbazone) obtained in Example 2 was dissolved in a 0.1 M acetate buffer (pH, 5.0) to make a concentration of $10^{-3}$ M. To the resulting solution (10 ml), an ion-exchange resin adsorbed Sn$^{++}$ ion thereon (5.5 μg of tin ion per 1 mg of the resin; 4 mg) was added, and the resultant mixture was filled in an ampoule. After replacement of the air above the solution in the ampoule by nitrogen gas, the ampoule was sealed.

EXAMPLE 6

Preparation of the radioactive diagnostic agent

The non-radioactive carrier obtained in Example 3 (1 ml) was admixed with an aqueous solution of gallium chloride-$^{67}$Ga solution (1 mCi/ml; pH, about 2) (1 ml) under an aseptic condition, and the resultant mixture was passed through a microfilter and filled in a vial. After replacement of the air above the solution in the vial by nitrogen gas, the vial was sealed.

The radioactive diagnostic agent as prepared above was subjected to paper chromatography (Toyo Filter Paper No. 51) using 80% methanol as the developing solvent. After development, scanning was carried out with a radiochromatoscanner. In the radioactivity chart, a main peak was observed at an Rf value of about 0.6, and a small peak probably due to unlabeled gallium chloride-$^{67}$Ga was present near the original point. By the radiochromatogram and the coloring method with a cuprous salt solution, it was confirmed that the nearly entire amount of the radioisotope forms a chelate compound with GBT.

EXAMPLE 7

Preparation of the radioactive diagnostic agent

The non-radioactive carrier obtained in Example 5 (1 ml) was admixed with an aqueous solution of sodium pertechnetate-$^{99m}$Tc solution (10 mCi/ml; pH, 5.5) (1 ml) under an aseptic condition, and the resultant mixture was passed through a microfilter and filled in a vial. After replacement of the air above the solution in the vial by nitrogen gas, the vial was sealed.

The radioactive diagnostic agent as prepared above was subjected to thin layer chromatography using silica gel (Merck G, 0.25 mm thick) as the adsorbent and 80% acetone as the developing solvent. After the development, scanning was carried out with a radiochromatoscanner. In the radioactivity chart, a main peak was observed at an Rf value of about 0.9. Besides, a small peak probably due to $^{99m}$Tc labeled tin colloid was seen at the original point, and a small peak due to an unidentified compound was present at an Rf value of about 0.7. By the radiochromatogram and the coloring method with a cuprous salt solution, it was confirmed that the nearly entire amount of the radioisotope forms a chelate compound with GBT.

EXAMPLE 8

Relationship between the amount of $Sn^{++}$ ion in the non-radioactive carrier and the property of the $^{99m}$Tc-labeled radioactive diagnostic agent prepared by the use of said non-radioactive carrier Non-radioactive carriers were prepared in the same manner as in Example 5 but using different amounts of $Sn^{++}$ ion. Using those non-radioactive carriers, there were prepared $^{99m}$Tc -labeled radioactive diagnostic agents in the same manner as in Example 7. As to the thus prepared $^{99m}$Tc-labeled radioactive diagnostic agents, chromatographic examination was carried out in the same manner as in Example 7. The results are shown in Table 1 wherein the numerals indicate the relative radioactivity values (%).

TABLE 1

| Peak | Amount of $Sn^{++}$ used (μg)*1 | | | | | | |
|---|---|---|---|---|---|---|---|
| | 0.5 | 1.0 | 1.5 | 5.5 | 11 | 55 | 550 |
| Rf = 0.9 | 86.9 | 95.7 | 93.3 | 90.3 | 87.5 | 78.0 | 72.4 |
| Rf = 0.7 | 1.9 | 1.9 | 2.3 | 3.4 | 4.1 | 4.4 | 3.7 |
| Original point | 11.2 | 2.3 | 4.4 | 6.3 | 8.4 | 17.6 | 23.9 |

Note:
*1Amount of $Sn^{++}$ ion per 1 ml of the non-radioactive carrier calculated from the amount of $Sn^{++}$ ion adsorbed on the ion-exchange resin.

From the above results, it is understood that when the amount of $Sn^{++}$ ion in the non-radioactive carrier is at least from 0.5 to 550 μg per 1 ml of the $10^{-3}$ m GBT solution, the $^{99m}$Tc-labeled radioactive diagnostic agent can be produced with a good efficiency. Taking the production rate of the major component into consideration, the amount of $Sn^{++}$ ion is preferred to be from 1 to 5.5 μg.

EXAMPLE 9

Distribution of the $^{99m}$Tc-labeled radioactive diagnostic agent in rabbit

Into each of nembutal-anesthetized rabbits, 0.2 ml of the $^{99m}$Tc -labeled radioactive diagnostic agent (containing the radioactivity of 1 mCi) was administered at the auricular vein, and continuous imaging with a scintillation camera was carried out. Regions of interest were provided in brain, heart, left kidney and lung, and the relative values of the radioactivies in brain and in other organs were measured. The results are shown in Table 2.

TABLE 2

| Item | Time after administration (sec) | | | | | |
|---|---|---|---|---|---|---|
| | 10 | 20 | 30 | 60 | 120 | 240 |
| Brain/Heart | 5.3 | 3.1 | 1.9 | 1.0 | 0.6 | 0.5 |
| Brain/Left kidney | 41.0 | 15.2 | 4.0 | 2.3 | 1.7 | 1.0 |
| Brain/Lung | 1.5 | 3.3 | 2.5 | 2.7 | 2.4 | 2.0 |

From the above results, it is understood that the radioactive diagnostic agent of the invention can pass through the blood-brain barrier immediately after the administration to accumulate in brain, and the amount of accumulation in brain is much higher than that in other organs. Thus, it is quite useful for imaging of brain as well as dynamic study of brain.

EXAMPLE 10

Toxicity of the $^{67}$Ga- or $^{99m}$Tc-labeled radioactive diagnostic agent

The $^{67}$Ga- or $^{99m}$Tc -labeled radioactive diagnostic agent obtained in Example 6 or 7 was attenuated radioactively to an appropriate extent and then administered intravenously to groups of SD strain male and female rats, each group consisting of 10 rats, at a dose of 1 ml per 100 g of the bodyweight (which corresponds to 300 times of the amount to be usually administered to human beings) or to groups of ICR strain male and female mice, each group consisting of 10 mice, at a dose of 0.5 ml per 10 g of the bodyweight (which corresponds to 1500 times of the amount to be usually administered to human beings). For the control groups, the same volume of physiologically saline solution as above was intravenously administered. All the groups were bred for 10 days, and the variation of the bodyweight was recorded everyday. No significant difference was observed between the medicated groups and the control groups. After the observation over 10 days, all the animals were sacrificed, and any abnormality was not observed on any organ taken out from them. Thus, it is understood that the toxicity of the $^{67}$Ga- or $^{99m}$Tc -labeled radioactive diagnostic agent is extremely low.

What is claimed is:

1. A radioactive diagnostic agent, comprising: a chelate of glucosone-bis(thio-semicarbazone), of the formula:

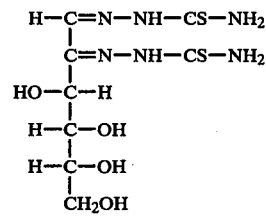

and a radioactive element selected from the group consisting of indium, galium and technetium.

2. A radioactive diagnostic composition suitable for use in medical diagnosis, comprising:
    a chelate of glucosone-bis(thio-semicarbazone) according to claim 1, and a pharmaceutically acceptable carried therefor 3. The composition of claim 2, which further includes an oxidizing agent.

4. The composition of claim 3, which further includes a reducing agent.

5. The composition of claim 2, in the form of an aqueous solution.

6. The composition of claim 2, in the form of a lyophilized powder.

7. A method for imaging body organs, comprising the step of:
    administering to said body a composition comprising a radioactive diagnostic agent chelate compound which includes a non-radioactive carrier having as an essential component glucosone-bis(thiocarbazone) of the formula:

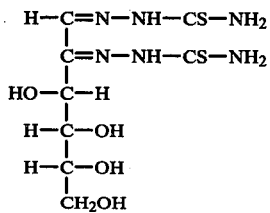

and a radioactive element; and a pharmaceutically acceptable carier therefor; and imaging said body organs.

8. A method according to claim 7, wherein said composition contains a reducing agent.

9. The method according to claim 7, wherein said composition contains an oxidizing agent.

10. The method according to claim 7, which comprises the step of imaging the brain of said body.

11. The method according to claim 8, which comprises the step of imaging the brain of said body.

12. The method according to claim 9, which comprises the step of imaging the brain of said body.

13. The method according to claim 7, wherein said radioactive element is selected from the group consisting of indium, galium and technetium.

* * * * *